(12) United States Patent
Pettigrew et al.

(10) Patent No.: US 6,836,974 B1
(45) Date of Patent: Jan. 4, 2005

(54) FIBER THICKNESS GAUGING SYSTEM AND METHOD

(76) Inventors: Victoria I. Pettigrew, 18640 Castle Lake Dr., Morgan Hill, CA (US) 95037; Stephen H. Pettigrew, 18640 Castle Lake Dr., Morgan Hill, CA (US) 95037

( * ) Notice: Subject to any disclaimer, the term of this patent is extended or adjusted under 35 U.S.C. 154(b) by 0 days.

(21) Appl. No.: 10/318,556

(22) Filed: Dec. 12, 2002

(51) Int. Cl.⁷ .................................................. G01B 5/02
(52) U.S. Cl. ............................ 33/566; 33/562; 33/1 BB
(58) Field of Search ................................ 33/566, 1 BB, 33/1 B, 562, 563, 732, 733, 735; 73/866; 702/81, 127, 128, 155, 170

(56) References Cited

U.S. PATENT DOCUMENTS

| | | | | | |
|---|---|---|---|---|---|
| 2,376,811 A | * | 5/1945 | Rigby | .......................... | 33/1 B |
| 3,099,089 A | * | 7/1963 | Bond et al. | ................... | 33/1 G |
| 4,697,346 A | * | 10/1987 | Warburg | ..................... | 33/1 BB |
| 5,400,513 A | * | 3/1995 | Duffield | ....................... | 33/1 B |
| 5,539,675 A | * | 7/1996 | Carroll Sr. et al. | ......... | 702/170 |
| 6,025,727 A | * | 2/2000 | Inkpen et al. | ................ | 702/127 |
| 6,629,051 B2 | * | 9/2003 | Tanaka | ........................ | 702/81 |

* cited by examiner

Primary Examiner—Christopher W. Fulton
(74) Attorney, Agent, or Firm—Zilka-Kotab, PC

(57) ABSTRACT

A system and method are provided for gauging a thickness of fiber. Included is a structure including a plurality of indicators and a plurality of numerical indicia. Such indicators each have a unique uniform thickness. Moreover, the numerical indicia each indicate a number of units of thickness (i.e. wraps per inch, etc.) correlating with the uniform thickness of the associated one of the indicators.

14 Claims, 6 Drawing Sheets

FIBER THICKNESS GAUGING SYSTEM AND METHOD

FIELD OF THE INVENTION

The present invention relates to fiber spinning, and more particularly to gauging a thickness of fiber during spinning.

BACKGROUND OF THE INVENTION

In conventional spinning practice, single fibers are spun and used as basic building blocks in the manufacture of the more complex fiber structures. Prior to the spinning process, fibers, which can be of natural or synthetic origin, are processed using various steps including, but not limited to carding, gilling, combing, drawing and roving. Such fibers may be extracted from various animals (i.e. alpacas, llamas, dogs, cats, etc.).

The prepared fiber is then creeled in a spinning frame where it is subjected first to a draft, or attenuation, by which the linear density of the fiber is reduced to a required level, and is then twisted with an amount of twist which depends upon the thickness of the fiber and its intended use. The spinning operation is normally carried out on a machine such as a ringframe, a cap-frame or a flyer-frame, in which the rotation of a spindle serves to both insert twist into the fiber and to wind the fiber onto a package carried on the spindle.

During the spinning operation, it is imperative that the fiber be spun with a consistent thickness for both aesthetic and durability purposes. The unit commonly employed for gauging fiber thickness during spinning is "wraps per inch."

Prior Art FIG. 1 illustrates a device 100 commonly employed to measure the number of wraps per inch associated with fiber being spun. As shown, the device 100 has a substantially rigid planar configuration including a mid portion 102 having a first width, and a pair of end portions 104 having a second width greater than the first width. For reasons that will soon become apparent, the mid portion 102 has a length of one (1) inch.

In use, fiber being spun must be wrapped about the mid portion 102 of the device 100 such that each wrapped portion abuts an adjacent wrapped portion. See Prior Art FIG. 2. Thus, the number of wraps of the fiber 200 that can fit between the end portions 104 indicates a number of wraps per inch.

Unfortunately, it is cumbersome to wrap and remove the fiber 200 using the device 100, as it this must be done manually. Furthermore, since the thickness gauging process must be carried out frequently during the spinning process, the necessary gauging may add a significant amount of time to the fiber spinning process.

DISCLOSURE OF THE INVENTION

A system and method are provided for gauging a thickness of fiber. Included is a structure including a plurality of indicators and a plurality of numerical indicia. Such indicators each have a unique uniform thickness. Moreover, the numerical indicia each indicate a number of units of thickness (i.e. wraps per inch, etc.) correlating with the uniform thickness of the associated one of the indicators.

In one embodiment, the structure may include a card. Such card may be transparent and the indicators may be opaque. Still yet, the indicators may include lines.

In another embodiment, the structure may include a table including information such as textual descriptions of different fiber thicknesses, ranges of wraps per inch each associated with a corresponding fiber thickness, amounts of yards per ounce each associated with a corresponding fiber thickness, and/or recommended ranges of needle sizes each associated with a corresponding fiber thickness.

As an option, a plurality of structures may be provided including a first structure for gauging the thickness of single-ply fiber and a second structure for gauging the thickness of double-ply fiber. As a further option, the structures may be connected.

A method is thus provided for gauging a thickness of fiber. Initially, a fiber is matched against one of a plurality of indicators each having a unique uniform thickness. Next, numerical indicia associated with the matched indicator is read for indicating a number of units of thickness (i.e. wraps per inch, etc.) correlating with the fiber.

Another apparatus is provided for gauging a thickness of fiber. The present structure is equipped with a uniform width including a pair of markings spaced one inch apart along a dimension parallel with a central axis of the structure. As an option, such structure may be substantially cylindrical.

Still another system and method are provided for performing various fiber-related calculations, utilizing a computer. Included is computer code for receiving input data such as an amount of spun fiber, an amount of raw fiber (not spun), and a thickness of the fiber when spun. Further provided is computer code for calculating output data such as an amount of spun fiber, an amount of raw fiber (not spun), and a thickness of the fiber when spun; based on the input data. Still yet, computer code is provided for outputting the output data.

BRIEF DESCRIPTION OF THE DRAWINGS

Prior Art

DESCRIPTION OF THE PREFERRED EMBODIMENTS

Figure 1:
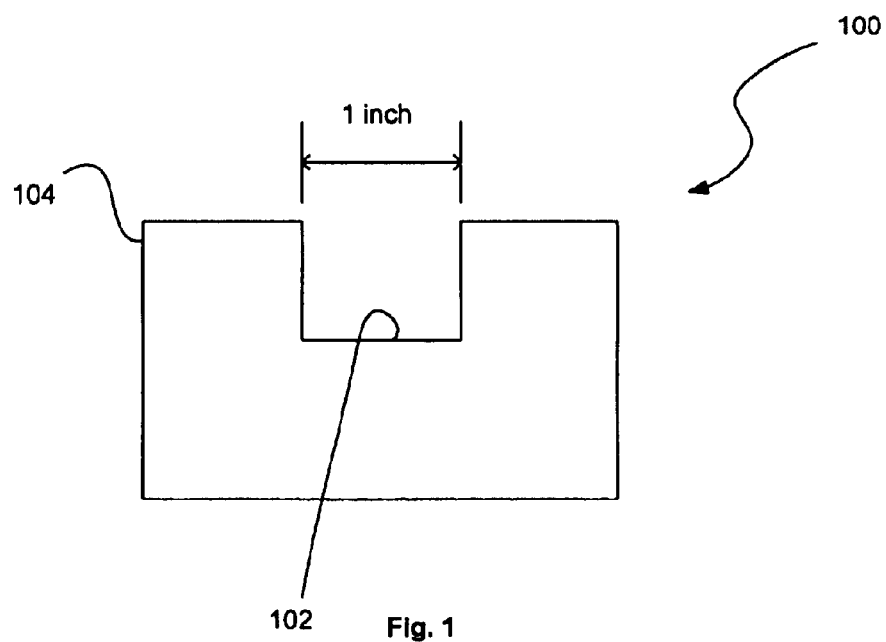
FIGS. 1 and 2 illustrate a device commonly employed to measure the number of wraps per inch associated with fiber being spun, in accordance with the prior art.
Figure 2:
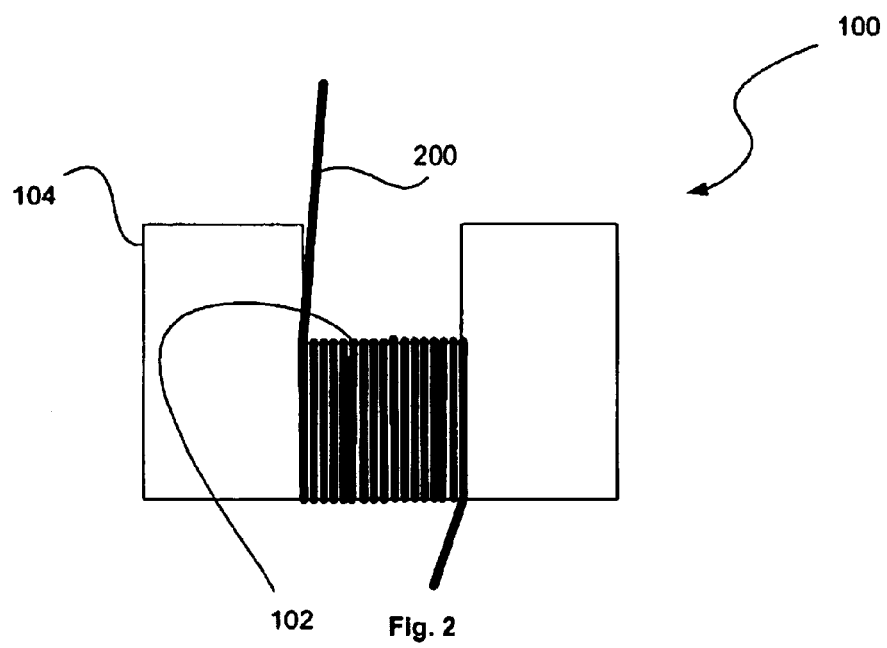
Figure 3:
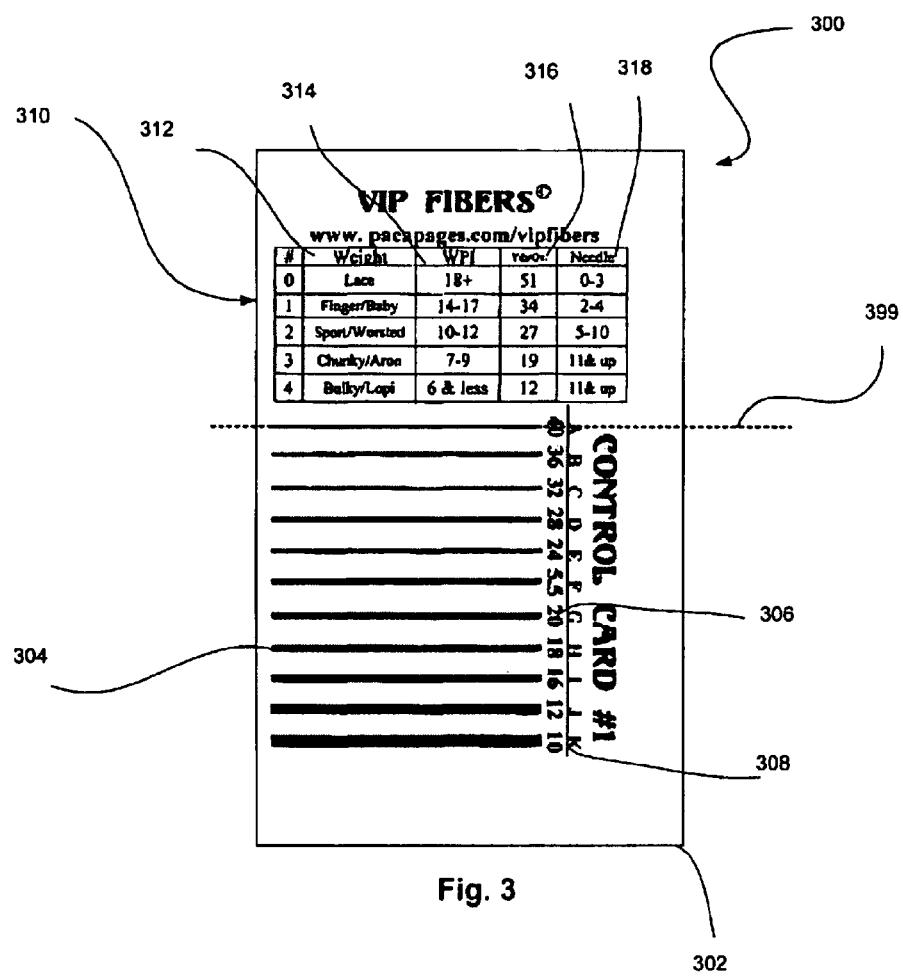
FIG. 3 illustrates a system for gauging a thickness of single-ply fiber, in accordance with one embodiment.

Prior art FIGS. 1–2 illustrate the prior art. FIG. 3 illustrates a system 300 for gauging a thickness of single-ply fiber, in accordance with one embodiment. In the context of the present description, the fiber may include any synthetic fiber or natural fiber (i.e. alpaca, llama, dog, cat, etc.) capable of being spun for use in garments, etc.

As shown, a structure is provided including a first resilient transparent card 302 with a substantially planar rectangular configuration. Of course, the card 302 need not necessarily be transparent. Such first resilient transparent card 302 defines a front face and a rear face with a periphery. This periphery includes a pair of long edges and a pair of short edges.

The front face of the first resilient transparent card 302 includes a plurality of parallel opaque lines 304 extending between the long edges of the first resilient transparent card 302 and in parallel with the short edges. Each opaque line 304 of the first resilient transparent card 302 has a unique uniform thickness.

Further, numerical indicia 306 is provided with each opaque line 304. Such numerical indicia 306 is adapted for indicating a number of single-ply wraps per inch correlating with the uniform thickness of the associated opaque line 304. Of course, any units of thickness may be used that describe a thickness of the fiber. Just by way of example, a number of wraps per centimeter may be used, actual thickness, etc. Still yet, alphabetic indicia 308 unique to the associated opaque line 304 is provided for reasons that will become apparent hereinafter.

The front face of the first resilient transparent card 302 further includes a table 310. Such table 310 includes a first column 312 with a plurality of textual descriptions of different fiber thicknesses. A second column 314 is included with a plurality of ranges of wraps per inch each associated with the corresponding fiber thickness. Still yet, a third column 316 is included with a plurality of amounts of yards per ounce each associated with the corresponding fiber thickness. Finally, a fourth column 318 shows a plurality of recommended ranges of needle sizes each associated with the corresponding fiber thickness. As an option, another column may be provided for indicating a numerical identifier, as shown.

In the context of the present description, any structure may be employed in lieu of a card which is capable of including indicators and a plurality of numerical indicia, where the numerical indicia may be used to indicate a number of units of thickness (i.e. number of wraps per inch) correlating with the uniform thickness of the associated one of the indicators. Moreover, such indicators may include any type of visual or tactile entity with thickness capable of being compared with that of fiber. To this end, a user may determine the thickness of the fiber in a fast, efficient manner.

Figure 4:
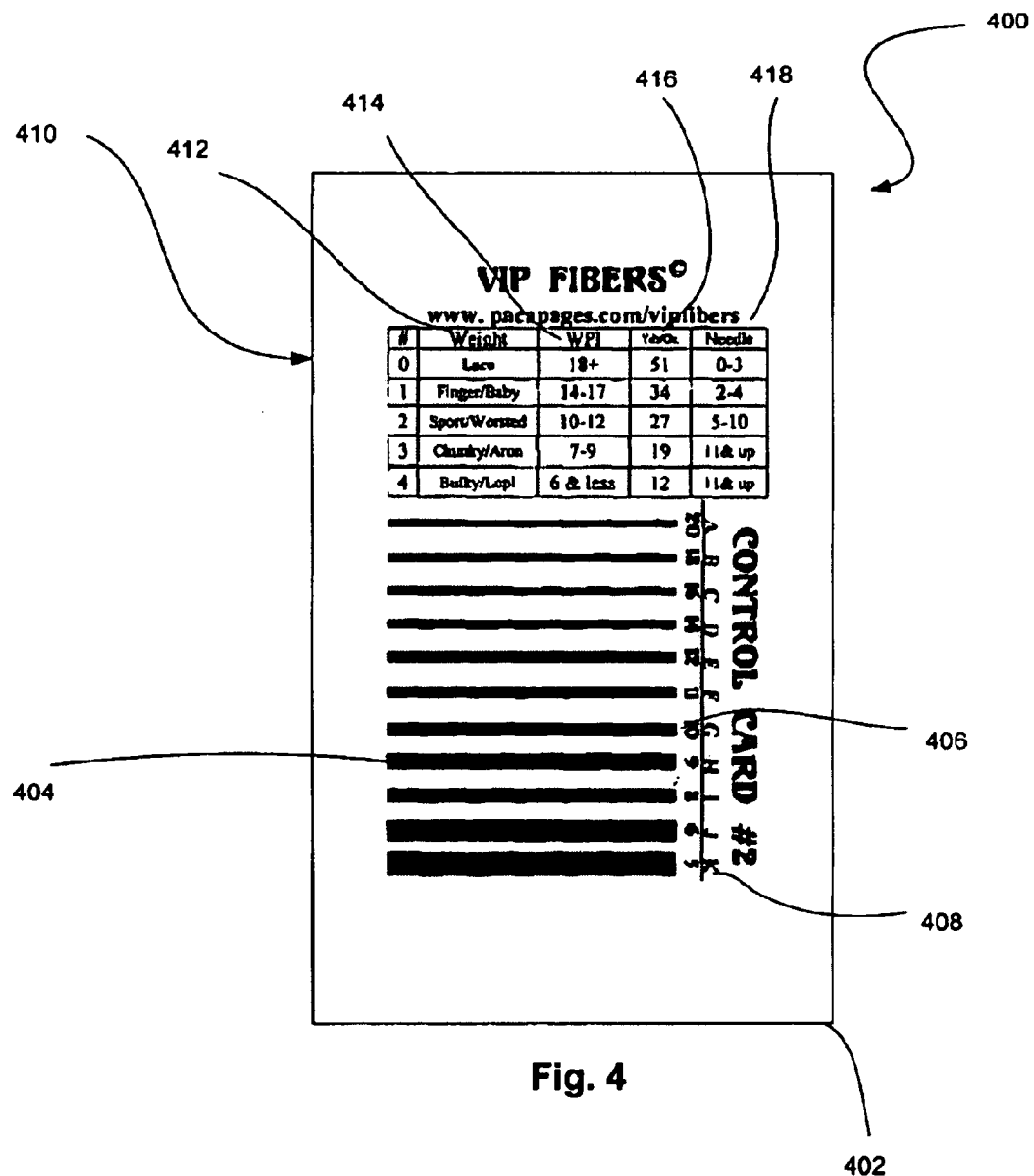
FIG. 4 illustrates a system for gauging a thickness of double-ply fiber, in accordance with one embodiment.

FIG. 4 illustrates a system 400 for gauging a thickness of double-ply fiber, in accordance with one embodiment. As shown, a structure is provided including a second resilient transparent card 402 with a substantially planar rectangular configuration. Such second resilient transparent card 402 defines a front face and a rear face with a periphery. This periphery includes a pair of long edges and a pair of short edges. Optionally, the first resilient transparent card 302 may be connected to the second resilient transparent card 402 via a string or the like.

Similar to the system 300 of FIG. 3, the front face of the second resilient transparent card 402 includes a plurality of parallel opaque lines 404 extending between the long edges of the second resilient transparent card 402 and in parallel with the short edges. Each opaque line 404 of the second resilient transparent card 402 has a unique uniform thickness.

Still yet, numerical indicia 406 is provided with each opaque line 404. Such numerical indicia 406 is adapted for indicating a number of double-ply wraps per inch correlating with the uniform thickness of the associated opaque line 404. Alphabetic indicia 408 unique to the associated opaque line 404 is also provided.

Such alphabetic indicia 408 corresponds to the alphabetic indicia 308 of the first resilient transparent card 302. By this design, a user may first identify a desired double-ply fiber thickness. This may be accomplished, for example, by matching the appropriate opaque line 404 of the second resilient transparent card 402 with a picture of a strand of double-ply spun fiber in a magazine. Then, when spinning the single-ply fiber to be used later for the double-ply fiber, the user may use the alphabetic indicia 308 & 408 to find the appropriate single-ply opaque line 304 of the first resilient transparent card 302 for gauging the thickness of the single-ply fiber.

The front face of the second resilient transparent card 402 further includes a table 410. Such table 410 includes a first column 412 with a plurality of textual descriptions of different fiber thicknesses. A second column 414 is included with a plurality of ranges of wraps per inch each associated with the corresponding fiber thickness. Still yet, a third column 416 is included with a plurality of amounts of yards per ounce each associated with the corresponding fiber thickness. Finally, a fourth column 418 shows a plurality of recommended ranges of needle sizes each associated with the corresponding fiber thickness. As an option, another column may be provided for indicating a numerical identifier, as shown.

Figure 5:
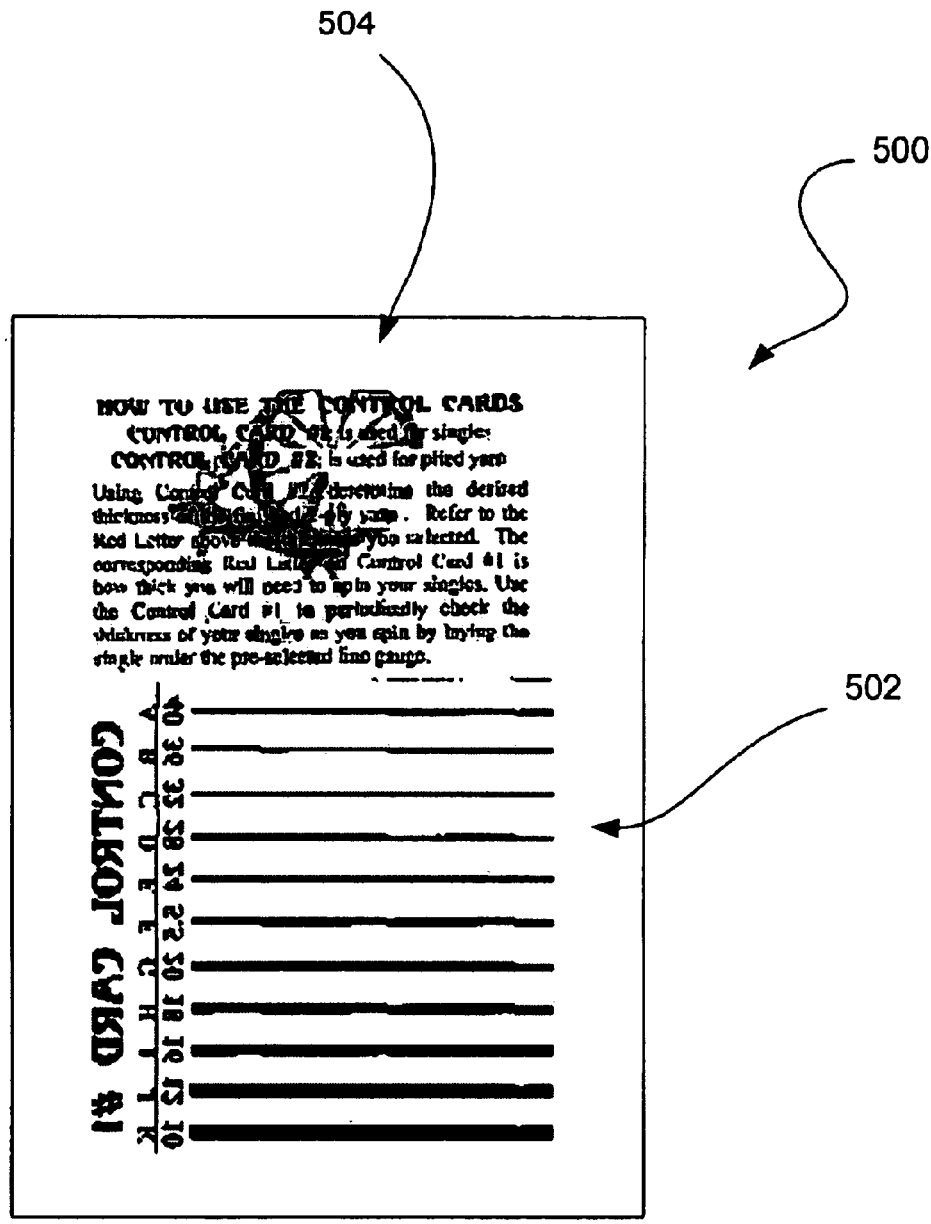
FIG. 5 illustrates a rear face of the first and second resilient transparent cards of FIGS. 3 and 4, in accordance with one embodiment.

FIG. 5 illustrates a rear face 500 of the first and second resilient transparent cards of FIGS. 3 and 4, in accordance with one embodiment. As shown, the rear face 500 has instructions 504 positioned thereon opposite the table on the front face of the associated resilient transparent card. As further shown, due to the transparency of the card, the opaque lines 502 may be viewed from the rear face 500.

In use, spun fiber is capable of being positioned adjacent one of the opaque lines representing a desired thickness, as indicated by the numerical indicia. See 399 of FIG. 3. The user may then adjust the spinning to either reduce or augment the thickness of the spun fiber to maintain the appropriate amount. When a thickness is simply not known, spun fiber is capable of being positioned adjacent one of the opaque lines (see 399 of FIG. 3) for comparison therewith, in order to match the spun fiber with one of the opaque lines with a similar thickness. Once a match has been made, numerical indicia associated with the matching opaque line may be used to indicate a thickness (i.e. wraps per inch, etc.) of the spun fiber for reference purposes. Moreover, such numerical indicia may be correlated with the table of one of the resilient transparent cards.

To this end, a user need not wrap the fiber about a device such as that shown in FIGS. 1–2. A more efficient, effective system of gauging a thickness or weight of a fiber is thus provided.

Figure 6:
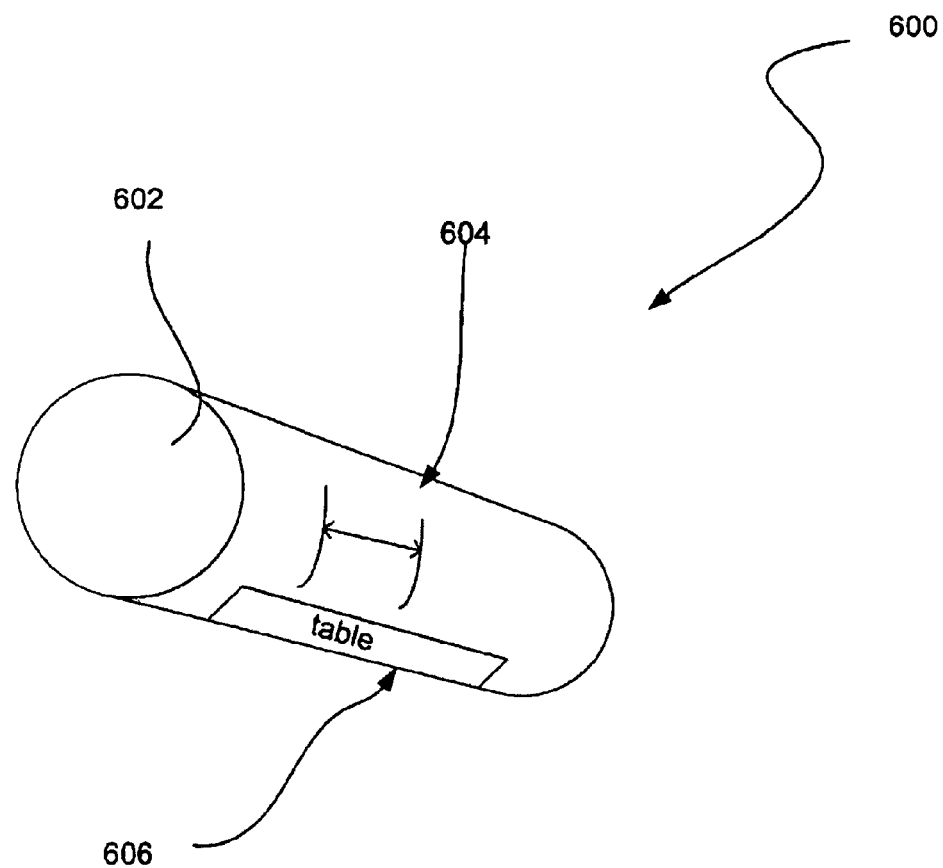
FIG. 6 illustrates a substantially cylindrical single-ply gauge, in accordance with another embodiment.

FIG. 6 illustrates a substantially cylindrical single-ply gauge 600, in accordance with another embodiment. As shown, the present gauge 600 includes a solid cylinder 602 defining a peripheral face and a pair of end faces. Such peripheral face of the cylinder 602 includes a pair of markings 604 spaced one inch apart along a dimension parallel with a central axis of the cylinder 602. Moreover, the peripheral face of the cylinder 602 is further equipped with a table 606 similar to that of FIGS. 2 and 3.

Specifically, such table 606 includes a plurality of columns similar to those of the cards of FIGS. 4–5, except that the table is wrapped about the peripheral face of the cylinder 602.

For example, a first column is provided with a plurality of textual descriptions of different fiber thicknesses. A second column is included with a plurality of ranges of wraps per inch each associated with the corresponding fiber thickness. Still yet, a third column is included with a plurality of amounts of yards per ounce each associated with the corresponding fiber thickness. Finally, a fourth column shows a plurality of recommended ranges of needle sizes each associated with the corresponding fiber thickness.

In use, spun fiber is capable of being wrapped about the cylinder 602 between the pair of markings 604 for indicating a thickness of the spun fiber for references purposes and for correlating with the table of the cylinder 602. Thus, unlike the prior art device of FIGS. 1–2, the spun fiber may be conveniently removed by pulling an end of the fiber in a direction parallel with the central axis of the cylinder 602.

Figure 7:
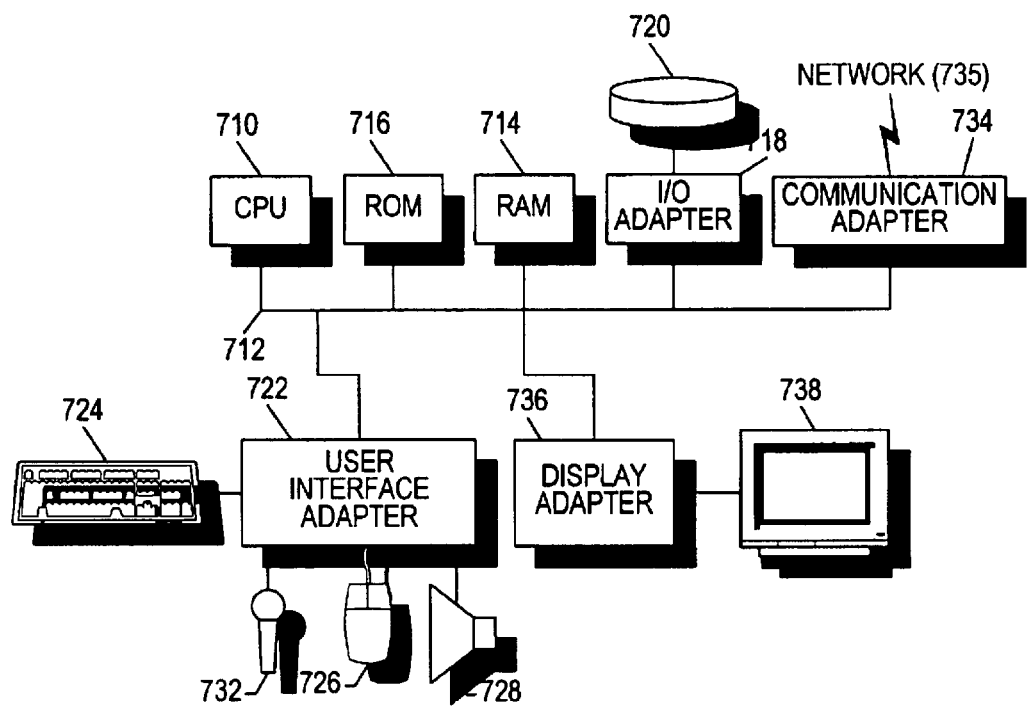
FIG. 7 shows a representative computer capable of processing fiber-related data, in accordance with another embodiment.

FIG. 7 shows a representative computer 702 capable of processing fiber-related data, in accordance with another embodiment. Such figure illustrates a typical hardware configuration of a computer in accordance with a preferred embodiment having a central processing unit 710, such as a microprocessor, and a number of other units interconnected via a system bus 712.

The computer shown in FIG. 7 includes a Random Access Memory (RAM) 714, Read Only Memory (ROM) 716, an I/O adapter 718 for connecting peripheral devices such as disk storage units 720 to the bus 712, a user interface adapter 722 for connecting a keyboard 724, a mouse 726, a speaker 728, a microphone 732, and/or other user interface devices such as a touch screen (not shown) to the bus 712, communication adapter 734 for connecting the computer to a communication network 735 (e.g., a data processing network) and a display adapter 736 for connecting the bus 712 to a display device 738.

The computer may have resident thereon an operating system such as the Microsoft® Windows® NT or Windows®/95 Operating System (OS), the IBM® OS/2® operating system, the MAC® OS, or UNIX™ operating system. It will be appreciated that a preferred embodiment may also be implemented on platforms and operating systems other than those mentioned. A preferred embodiment may be written using JAVA, C, and/or C++ language, or other programming languages, along with an object oriented programming methodology. Object oriented programming (OOP) has become increasingly used to develop complex applications.

Our course, the various embodiments set forth herein may be implemented utilizing hardware, software, or any desired combination thereof. For that matter, any type of logic may be utilized which is capable of implementing the various functionality set forth herein.

In use, the computer is adapted for receiving input data such as an amount of spun fiber, an amount of raw fiber (not spun), and/or a thickness of the fiber when spun. With this information, output data is calculated including an amount of spun fiber, an amount of raw fiber (not spun), and a thickness of the fiber when spun. Once calculated, such output data may be outputted via a display or the like. Table 1 illustrates an exemplary relationship between the foregoing values, which may be used to calculate the output data. It should be noted that such empirical correlations were unexpected results from experiments.

TABLE #1

| # | Weight | WPI | Yds/Oz. | Needle |
|---|--------|-----|---------|--------|
| 0 | Lace | 18+ | 51 | 0–3 |
| 1 | Finger/Baby | 14–17 | 34 | 2–4 |
| 2 | Sport/Worsted | 10–12 | 27 | 5–10 |
| 3 | Chunky/Aron | 7–9 | 19 | 11 & up |
| 4 | Bulky/Lopi | 6 & less | 12 | 11 & up |

For example, if the input data includes an amount of raw fiber (not spun) including 1 ounce, and a thickness of the fiber when spun equal to 15 wraps/inch, the output data may indicate that approximately 24 yards of spun fiber will be available. In another example, the input data may include just a thickness of the fiber when spun equal to 11. In such example, the output may simply be 27 yards/ounce. In still yet another example, a user may enter as input data that he or she wishes to generate 102 yards of spun fiber and that the thickness will be 18 wraps/inch. The output data would thus indicate that 2 ounces of unspun fiber is required. Of course, any desired output data may be calculated based on the input data and the relationship set forth in Table 1.

Optionally, the units may be user-defined. Of course, various interpolation techniques may be used to refine the various ranges set forth in Table 1.

While various embodiments have been described above, it should be understood that they have been presented by way of example only, and not limitation. Thus, the breadth and scope of a preferred embodiment should not be limited by any of the above described exemplary embodiments, but should be defined only in accordance with the following claims and their equivalents.

What is claimed is:

1. A system for gauging a thickness of fiber, comprising:

a single-ply gauge including a first resilient transparent card with a substantially planar rectangular configuration defining a front face and a rear face with a periphery including a pair of long edges and a pair of short edges, the front face of the first resilient transparent card including a plurality of parallel opaque lines extending between the long edges of the first resilient transparent card and in parallel with the short edges, each opaque line of the first resilient transparent card having a unique uniform thickness, numerical indicia indicating a number of single-ply wraps per inch correlating with the uniform thickness of the associated opaque line, and an alphabetic indicia unique to the associated opaque line; the front face of the first resilient transparent card further including a table including a first column with a plurality of textual descriptions of different fiber thicknesses, a second column with a plurality of ranges of wraps per inch each associated with the corresponding fiber thickness, a third column with a plurality of amounts of yards per ounce each associated with the corresponding fiber thickness, and a fourth column with a plurality of recommended ranges of needle sizes each associated with the corresponding fiber thickness; the rear face of the first resilient transparent card having instructions positioned thereon opposite the table on the front face of the first resilient transparent card, whereby spun fiber is capable of being positioned adjacent the opaque lines of the first resilient transparent card for comparison therewith in order to match the spun fiber with one of the opaque lines with a similar thickness, wherein the numerical indicia associated with the matching opaque lines indicates a thickness of the spun fiber for references purposes and for correlating with the table of the first resilient transparent card;

a double-ply gauge including a second resilient transparent card with a substantially planar rectangular configuration defining a front face and a rear face with a periphery including a pair of long edges and a pair of short edges, the front face of the second resilient transparent card including a plurality of parallel opaque lines extending between the long edges of the second resilient transparent card and in parallel with the short edges, each opaque line of the second resilient transparent card having a unique uniform thickness, numerical indicia indicating a number of double-ply wraps per inch correlating with the uniform thickness of the associated opaque line, and an alphabetic indicia unique to the associated opaque line and corresponding to the alphabetic indicia of the first resilient transparent card; the front face of the second resilient transparent card further including a table including a first column with a plurality of textual descriptions of different fiber thicknesses, a second column with a plurality of ranges of wraps per inch each associated with the corresponding fiber thickness, a third column with a plurality of amounts of yards per ounce each associated with the corresponding fiber thickness, and a fourth column with a plurality of recommended ranges of needle sizes each associated with the corresponding fiber thickness; the rear face of the second resilient transparent card having instructions positioned thereon opposite the table on the front face of the second resilient transparent card, whereby the spun fiber is capable of being positioned adjacent the opaque lines of the second resilient transparent card for comparison therewith in order to match the spun fiber with one of the opaque lines with a similar thickness, wherein the numerical indicia associated with the matching opaque lines indicates a thickness of the spun fiber for references purposes and for correlating with the table of the second resilient transparent card;

an additional single-ply gauge including a solid cylinder defining a peripheral face and a pair of end faces, the peripheral face of the cylinder including a pair of markings spaced one inch apart along a dimension parallel with a central axis of the cylinder, the peripheral face of the cylinder further including a table including a first column with a plurality of textual descriptions of different fiber thicknesses, a second column with a plurality of ranges of wraps per inch each associated with the corresponding fiber thickness, a third column with a plurality of amounts of yards per ounce each associated with the corresponding fiber thickness, and a fourth column with a plurality of recommended ranges of needle sizes each associated with the corresponding fiber thickness, whereby the spun fiber is capable of being wrapped about the cylinder between the pair of markings for indicating a thickness of the spun fiber for references purposes and for correlating with the table of the cylinder; and a computer including computer code for receiving input data selected from the group consisting of an amount of spun fiber, an amount of raw fiber, and a thickness of the fiber when spun; computer code for calculating output data selected from the group consisting of an amount of spun fiber, an amount of raw fiber, and a thickness of the fiber when spun; and computer code for outputting the output data.

2. An apparatus for gauging a thickness of fiber, comprising:

a structure including:

a plurality of indicators each having a unique uniform thickness, and a plurality of numerical indicia each indicating units of thickness correlating with the uniform thickness of the associated one of the indicators;

wherein the structure is substantially cylindrical.

3. The apparatus as recited in claim 2, wherein the indicators include lines.

4. The apparatus as recited in claim 2, wherein the structure includes a table including information selected from the group consisting of textual descriptions of different fiber thicknesses, a plurality of ranges of wraps per inch each associated with a corresponding fiber thickness, a plurality of amounts of yards per ounce each associated with a corresponding fiber thickness, and a plurality of recommended ranges of needle sizes each associated with a corresponding fiber thickness.

5. The apparatus as recited in claim 2, wherein a plurality of the structures are provided including a first structure for gauging the thickness of single-ply fiber and a second structure for gauging the thickness of double-ply fiber.

6. The apparatus as recited in claim 5, wherein the structures are connected.

7. A method for gauging a thickness of fiber, comprising:

matching fiber against one of a plurality of indicators each having a unique uniform thickness; and reading numerical indicia associated with the matched indicator for indicating units of thickness correlating with the fiber;

wherein the structure is substantially cylindrical.

8. The method as recited in claim 7, wherein the indicators include lines.

9. The method as recited in claim 7, wherein the structure includes a table including information selected from the group consisting of textual descriptions of different fiber thicknesses, a plurality of ranges of wraps per inch each associated with a corresponding fiber thickness, a plurality of amounts of yards per ounce each associated with a corresponding fiber thickness, and a plurality of recommended ranges of needle sizes each associated with a corresponding fiber thickness.

10. The method as recited in claim 7, wherein a plurality of the structures are provided including a first structure for gauging single-ply fiber and a second structure for gauging double-ply fiber.

11. An apparatus for gauging a thickness of fiber, comprising:

a structure with a uniform width including a pair of markings spaced one unit apart along a dimension parallel with a central axis of the structure;

wherein the structure includes a solid member defining a peripheral face and a pair of end faces, and the indicators and the numerical indicia are positioned on the peripheral face;

wherein the structure is substantially cylindrical.

12. The apparatus as recited in claim 11, wherein spun fiber is capable of being wrapped about the structure, which includes a cylinder, between the pair of markings for indicating a thickness of the spun fiber.

13. The apparatus as recited in claim 11, wherein the unit includes an inch.

14. The apparatus as recited in claim 11, wherein the structure includes a table including information selected from the group consisting of textual descriptions of different fiber thicknesses, a plurality of ranges of wraps per inch each associated with a corresponding fiber thickness, a plurality of amounts of yards per ounce each associated with a corresponding fiber thickness, and a plurality of recommended ranges of needle sizes each associated with a corresponding fiber thickness.

* * * * *